United States Patent [19]

Papantoniou et al.

[11] 4,272,511

[45] Jun. 9, 1981

[54] COSMETIC COMPOSITIONS FOR TREATING HAIR

[75] Inventors: Christos Papantoniou, Montmorency; Jean Mondet, Sevran, both of France

[73] Assignee: L'Oreal, Paris, France

[21] Appl. No.: 50,428

[22] Filed: Jun. 20, 1979

[30] Foreign Application Priority Data

Jun. 23, 1978 [FR] France .............................. 78 18832
Feb. 8, 1979 [FR] France .............................. 79 03260

[51] Int. Cl.³ .............................................. A61K 7/06
[52] U.S. Cl. ........................................ 424/47; 132/7; 424/70; 424/71; 424/78; 424/DIG. 1; 424/DIG. 2
[58] Field of Search .................. 424/DIG. 2, DIG. 1, 424/47, 70; 8/10–11, 127.51

[56] References Cited

U.S. PATENT DOCUMENTS

| | | | |
|---|---|---|---|
| 3,171,784 | 3/1965 | Witwer | 424/47 |
| 3,806,317 | 4/1974 | Papantoniou et al. | 424/DIG. 2 |
| 4,173,627 | 11/1979 | Dermain et al. | 424/47 |
| 4,192,862 | 3/1980 | Pengilly | 8/127.51 |

FOREIGN PATENT DOCUMENTS 2003487 1/1970 Fed. Rep. of Germany ............. 424/70

Primary Examiner—Ethel G. Love
Attorney, Agent, or Firm—Cushman, Darby & Cushman

[57] ABSTRACT

This invention relates to cosmetic tetrapolymer or higher polymer compositions useful as lacquers and setting lotions.

12 Claims, No Drawings

COSMETIC COMPOSITIONS FOR TREATING HAIR

This invention has for its object novel compositions particularly lacquers and setting lotions.

French Pat. No. 70.16821 already specifies for the making of lacquers and setting lotions, the use of copolymers resulting from copolymerization of 40 to 90% by weight of N-vinylpyrrolidone, 40 to 5% by weight of at least an acid vinyl ester having from 2 to 22 carbon atoms and 20 to 3% at least of an unsaturated carboxylic acid.

However, it was found upon use that these polymer, when used as resins in lacquers and setting lotions, result in a high powdering, i.e., the formation of white films which have the effect of making the hair unaesthetic. Moreover, because of the presence of a large proportion of N-vinylpyrrolidone, it was found that these resins led to considerable stickiness of the hair even in an atmosphere with a relatively low humidity.

It has now been found in an entirely surprising manner that the powdering effect can be eliminated by reducing not only the proportions of the N-vinylpyrrolidone but also by using crotonic acid or at least fourth monomer as other vinyl acetate monomers. The copolymers according to the invention are therefore tetrapolymers or higher polymers but preferably tetrapolymers.

Comparative tests made by the applicants on copolymers with different structure made it possible to show that the simultaneous presence in the polymers according to the invention of N-vinylpyrrolidone, crotonic acid vinyl acetate and another monomer, these monomers being present in well defined proportions, was essential to obtain copolymers exhibiting all the qualities required for making good lacquers and setting lotions not leading, upon use, to the powderng effect.

This invention has for its object as a novel industrial product is cosmetic composition particularly a lacquer or setting lotion containing in a suitable cosmetic vehicle at least a copolymer comprising groups resulting from copolymerization of:

(i) 1 to 30% and preferably 3 to 20% by weight of N-vinylpyrrolidone,
(ii) 13 to 87% and preferably 20 to 70% by weight of vinyl acetate,
(iii) 2 to 15% and preferably 3 to 12% by weight of crotonic acid, and
(iv) 1 to 80% and preferably 3 to 60% by weight of at least a fourth monomer, this latter preferably being selected from the group consisting of:
(a) vinyl esters corresponding to the following general formula:

$$CH_2=CH-O-\underset{\underset{O}{\|}}{C}-R_1 \qquad (I)$$

wherein:
$R_1$ represents a linear or branched alkyl radical having 1 to 21 carbon atoms,
(b) allyl and methallyl esters corresponding to the followng formula:

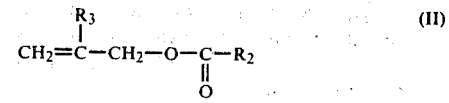

wherein:
$R_2$ represents a linear or branched alkyl radical having 1 to 21 carbon atoms and $R_3$ represents a hydrogen atom or a methyl radical,
(c) vinyl ethers corresponding to the following general formula:

$$CH_2=CH-O-R_4 \qquad (III)$$

wherein:
$R_4$ represents a linear or branched alkyl radical having 4 to 18 carbon atoms,
(d) alpha-olefins corresponding to the following formula:

$$CH_2=CH-(CH_2)_n-CH_3 \qquad (IV)$$

wherein:
n is an integer from 3 to 15 inclusive, and
(e) vinyl, allyl or methallyl esters of an α- or β-cyclic carboxylic acid corresponding to the following formula:

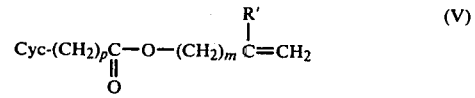

wherein:
R' represents a hydrogen atom or a methyl radical,
m is 0 or 1,
p is 0 or 1,
wherein p=0, Cyc represents a saturated or unsaturated mono- or polycyclic radical such as, for example:
(i) a radical of the formula:

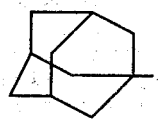

(ii) a radical of the formula:

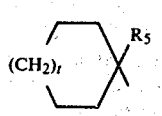

wherein:
$R_5$ represents a hydrogen atom or a methyl radical and t is 0 or 1,
(iii) a radical of the formula:

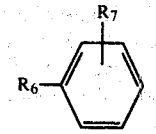

wherein:

$R_6$ represents a hydrogen atom, a methyl, ethyl, tert-butyl, ethoxy, butoxy or dodecoxy radical and $R_7$ represents a hydrogen atom, an alkyl radical of 1 to 4 carbon atoms or an alkoxy radical of 1 to 4 carbon atoms, or (iv) a radical of the formula:

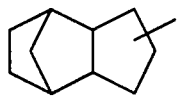

when p=1, Cyc represents a radical of formula:

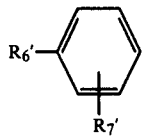

wherein:

$R'_6$ and $R'_7$ have the same signification as given above for $R_6$ and $R_7$.

Of the vinyl esters of formula (I) there can be cited in particular: vinyl esters of propionic, butyric, hexanoic, octanoic, decanoic, lauric, myristic, palimitic, stearic, isostearic, behenic, 2-ethyl hexanoic, 2,2-dimethyl propanoic, 2,2-dimethyl pentanoic, 2,2-dimethyl hexanoic, 2,2-dimethyl octanoic, 2,2-dimethyl decanoic, 2,2,4,4-tetramethyl valeric, 2-isopropyl 2,3-dimethyl butyric, 2-methyl 2-ethyl heptanoic, 2-methyl 2-propyl hexanoic, 2-methyl 2-isopropyl hexanoic, 3,5,5-trimethyl hexanoic acid and their isomers, and mixtures of some of these acids and particularly the mixture sold by the Shell Company under the tradename "Versatic Acid" and the mixtures sold by Ugine-Kuhlmann under the tradenames CEKANOIC $C_8$, $C_9$ and $C_{10}$ acids.

Of the allyl or methallyl esters of formula (II) there can be cited in particular allyl or methallyl esters of acetic, propionic, butyric, hexanoic, octanoic, decanoic, lauric, mystric, palmitic, stearic, isostearic, behenic, 2-ethyl hexanoic, 2,2-dimethyl propanoic, 2,2-dimethyl pentanoic, 2,2-dimethyl hexanoic, 2,2-dimethyl octanoic, 2,2-dimethyl decanoic, 2,2,4,4-tetramethyl valeric, 2-isopropyl 2,3-dimethyl butyric, 2-methyl 2-ethyl hexanoic, 2-methyl 2-propyl hexanoic, 2-methyl 2-isopropyl hexanoic, 3,5,5-trimethyl hexanoic acid and their isomers, and mixtures of some of these acids and particularly the mixture sold by Shell Company under the tradename "Versatic Acid" and the mixtures sold by Ugine-Kuhlmann under the tradenames CEKANOIC $C_8$, $C_9$ and $C_{10}$ acids.

Of the vinyl ethers of formula (III) there can be cited in particular: butyl vinyl ether, hexylvinylether, octyl-vinylether, decylvinylether, dodecylvinylether, hexadecylvinylether and octadecylvinylether.

Of the α-olefins of formula (IV) there can be cited in particular: 1-hexene, 1-octene, 1-decene, 1-dodecene and 1-octadecene.

Of the vinyl, allyl or methyallyl esters of formula (V) there can be cited in particular: the vinyl, allyl and methallyl esters of 1-adamantane carboxylic, cyclohexane carboxylic, cyclopentane carboxylic, benzoic, phenylacetic, 4-tertbutyl benzoic, cyclopentane, 1-methyl carboxylic, cyclohexane 1-methyl carboxylic, tricyclo[5.2.1.0$^{2,6}$]decane 3-carboxylic and tricyclo[5.2.1.0$^{2,6}$]decane 4-carboxylic acid, these two latter acids being sold, in mixture form by the Hoechst Company under the tradename TCD Carboxylic Acid S.

Although excellent results have been obtained with various monomers of formula (I) to (IV), it is preferred to use according to the invention those of formula (V) as the fourth monomer.

The copolymers according to the invention can be represented by the following general formula:

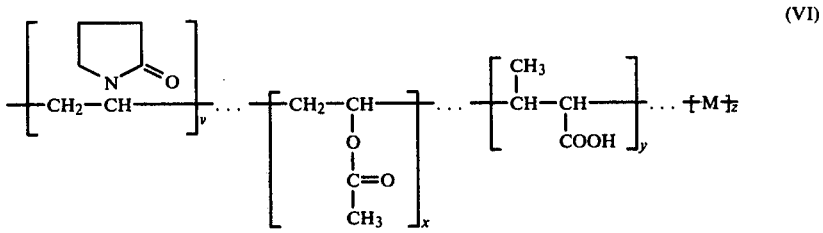

(VI)

wherein:

M represents a group of at least an unsaturated monomer such as those of formula (I) to (V) above, v representing from 1 to 30% by weight, x representing from 13 to 87% by weight, y representing from 2 to 15% by weight, and z representing from 1 to 80% by weight, v+x+y+z being equal to 100%.

According to a preferred form of the invention the copolymers are used in a form neutralized with an inorganic or organic base taken particularly from the group made up of: soda, potash, ammonia, monoethanolamine, diethanolamine, triethanolamine, isopropanolamine, diisopropanolamine, tri[(2-hydroxy) 1-propyl]amine, 2-amino 2-methyl 1-propanol, 2-amino 2-methyl 1,3-propanediol, 2-amino 2-hydroxymethyl 1,3-propanediol, said neutralization being able to be total or partial.

In a general way the copolymers according to the invention have an average molecular weight that can be between 2,000 and 100,000 and more particularly between 5,000 and 60,000, these molecular weights being average molecular weights of a number determined by osmometry.

Further these polymers have an absolute viscosity between 0.8 and 8 cPo and preferably between 1 and 6 cPo, measured in 5% solution in dimethylformanide (DMF) at 34.6° C.

According to the invention, the cosmetic compositions contain 0.5 to 10% by weight of at least a polymer as defined above.

The setting lotions according to the invention are present in the form of aqueous or dilute alcohol solutions containing from 20 to 70% by weight of alcohol and have a copolymer concentration preferably between 1 and 3% by weight.

The alcohols generally used for making setting lotions are preferably low molecular weight lower aliphatic alcohols such as ethanol or isopropanol.

These setting lotions can further contain various adjuvants such as, for example, plasticizers, perfumes, dyes, etc.

The hair lacquers according to the invention are obtained by putting in solution in an alcohol at least a copolymer as defined above, this solution being placed in an aerosol bomb and mixed with a propellant gas under pressure.

According to this embodiment, the copolymer is preferably in a proportion of 0.7 and 8% by weight.

The lacquers can also contain a third solvent which can be present in a proportion between 3 and 35% by weight.

The alcohol, which can be either ethanol or isopropanol, is generally present in a proportion between 5 and 80% and preferably 6 and 70% by weight.

Of the various third solvents that can be used in the lacquers, there can be cited in particular methylene chloride, trichloroethane, ethyl chloride, acetone, ethyl acetate and dichlorodifluoroethane.

As propellant there can be used fluorocarbons either alone, or in mixtures of themselves, particularly those sold under the tradename "Freon" and in particular "Freons 11, 12, 22, 133A and 142B."

It is also possible to use as the propellant carbon dioxide, nitrogen protoxide ($N_2O$), dimethylether, hydrocarbons such as propane, butane and isobutane, or possibly compressed air, these propellants being used alone or in mixtures of themselves or with one or more Freons such as those listed above.

The compositions according to the invention in the form of lacquers can also contain various ingredients generally used in this type of composition such as plasticizers, glossing agents, perfumes, dyes, restructuring agents and anionic, cationic or nonionic surfactants.

This invention also has for its object a setting process. According to this process, at least a lotion according to the invention is applied to the hair, then the hair is put up in curlers having a diameter of about 15 to 30 mm and the hair is subjected to a drying at a temperature on the order of 25° to 55° C.

The amount to be applied to the hair depends, of course, on the volume of the hair but it is generally on the order of 10 to 100 cc and preferably 20 to 50 cc.

According to a variant of the invention, the copolymers as described above can also be used in the compositions according to the invention in association with other polymers of an anionic or cationic nature, the compositions then being in the form of creams, gels, emulsions, etc.

According to this embodiment, the polymer of an anionic or cationic nature is present in the composition in a concentration between 0.10 and 10% and preferably between 0.02 and 5%.

According to this embodiment, the compositions can, of course, contain other ingredients such as those listed above.

The copolymers that can be used according to the invention are for the most part known and can easily be obtained by standard polymerization methods, i.e., either in solution in a solvent or in mass, or again in suspension in an inert liquid or emulsion. Another process called polymerization by precipitation consists in using a solvent in which the monomers are soluble but in which the polymer precipitates at the end of polymerization.

According to this process the polymer is isolated by filtering. Of the suitable solvents for this type of polymerization there can be cited cyclohexane, methylethylketone, heptane, ethyl acetate, etc. Of the copolymerization initiators there can be cited in particular azobisisobutyronitrile, peresters, percarbonates or redox systems. Of the peresters there can be cited in particular tertiobutyl 2-ethyl perhexanoate and tertiobutyl perpivalate.

The amount of the initiator is generally between 0.1 and 6% in relation to the total weight of the monomers used for copolymerization.

The copolymerization reaction is generally performed by heating under nitrogen and with agitation at a temperature of 55° to 85° C. The heating time is preferably between 6 and 24 hours.

For a better understanding of the invention there will now be described by way of illustration and without any limiting character several examples of preparation of copolymers and several examples of compositions in the form of lacquers or setting lotions.

EXAMPLES OF PREPARATION

EXAMPLE 1

In a 500-ml ballon flask were introduced under nitrogen atmosphere 66 g of vinyl acetate, 17.5 g of N-vinylpyrrolidone, 6.5 g of crotonic acid, 10 g of allyl stearate, 11 g of absolute ethanol and 0.5 of tertiobutyl peroxy 2-ethyl hexanoate. The reaction mixture was then heated for 18 hours at 70° C. At the end of the copolymerization reaction, the copolymer was precipitated in diethylether.

After the polymer was isolated, it was then dried under reduced pressure and exhibited an acid value of 59 and a viscosity of 3 cPo measured in a 5% solution in dimethylformamide at 34.6° C.

The copolymers of examples 3 to 7 were also prepared by the same mode of operation as described above.

EXAMPLE 2

Into a 500-ml ballon flask were introduced under nitrogen atmosphere 55 g of vinyl acetate, 15 g of N-vinylpyrrolidone, 5 g of crotonic acid, 25 g vinyl 4-tert-butyl benzoate, 100 g of ethyl acetate and 0.6 g of azobisisobutyronitrile.

The reaction mixture was then heated for 6 hours at 78° C.

After completion of the copolymerization reaction, the copolymer was precipitated in petroleum ether.

After the polymer was isolated, it was then dried under reduced pressure (yield: 60%) and exhibited an acid value of 32 and a viscosity of 1.5 cPo (5% solution in DMF at 34.6° C.).

According to the same mode of operation as that described in example 2 above, the copolymers of examples 8 to 22 of the following tables were prepared:

TABLE 1

| MONOMERS | Ex 3 | Ex 4 | Ex 5 | Ex 6 | Ex 7 | Ex 8 | Ex 9 | Ex 10 | Ex 11 | Ex 12 | Ex 13 | Ex 14 | Ex 15 |
|---|---|---|---|---|---|---|---|---|---|---|---|---|---|
| N-vinylpyrrolidone | 17.5 | 17.5 | 17.5 | 17.5 | 20 | 10 | 20 | 15 | 20 | 10 | 29 | 20 | 20 |
| Vinyl acetate | 71 | 66 | 66 | 66 | 67 | 67 | 65 | 67 | 13 | 65 | 13 | 22 | 61 |

TABLE I-continued

| MONOMERS | Ex 3 | Ex 4 | Ex 5 | Ex 6 | Ex 7 | Ex 8 | Ex 9 | Ex 10 | Ex 11 | Ex 12 | Ex 13 | Ex 14 | Ex 15 |
|---|---|---|---|---|---|---|---|---|---|---|---|---|---|
| Crotonic acid | 6.5 | 6.5 | 6.5 | 6.5 | 3 | 10 | 5 | 8 | 12 | 10 | 3 | 8 | 5 |
| Vinyl 4-tert butyl benzoate | | | | | 10 | 10 | | | 55 | | 40 | | |
| Vinyl benzoate | | | | | | | | 10 | | 5 | | | |
| Allyl 4-tert-butyl benzoate | | | | | | | 10 | | | | | | 4 |
| Vinyl stearate | | | | | | 3 | | | | | | 10 | 10 |
| Allyl benzoate | | | | | | | | | | | | 4 | |
| Allyl stearate | 5 | | | | | | | | | 10 | 15 | | |
| Vinyl Laurate | | 10 | | | | | | | | | | | |
| Vinyl 2,2-dimethyl octanoate | | | 10 | | | | | | | | | | |
| Vinyl 2,2-dimethyl pentanoate | | | | 10 | | | | | | | | | |
| Vinyl propionate | | | | | | | | | | | | 36 | |
| Acid value | 61 | 55 | 50 | 57 | 34 | 66 | 34 | 53 | 76 | 64 | 19 | 54 | 44 |
| Viscosity (5% in solution in DMF at 34.6° C.) | 2.91 | 2.95 | 2.87 | 2.98 | 2.82 | 1.45 | 1.63 | 1.42 | 1.29 | 1.65 | 1.35 | 1.48 | 1.67 |

TABLE II

| MONOMERS | Ex 16 | Ex 17 | Ex 18 | Ex 19 | Ex 20 | Ex 21 |
|---|---|---|---|---|---|---|
| N-vinylpyrrolidone | 20 | 10 | 30 | 25 | 20 | 15 |
| Vinyl acetate | 57 | 64 | 51 | 58 | 58 | 67 |
| Crotonic Acid | 10 | 10 | 3 | 3 | 8 | 5 |
| Vinyl phenylacetate | 5 | | | | | |
| Vinyl cyclohexanoate | | 6 | | | | |
| Vinyl 1-adamantane carboxylate | | | 6 | | | |
| Vinyl cyclopentanoate | | | | 6 | | |
| Vinyl 1-methyl cyclohexanoate | | | | | | 5 |
| Vinyl 1-methyl cyclopentanoate | | | | | 6 | |
| Allyl stearate | 8 | 10 | 10 | 8 | 8 | 8 |
| Acid value | 67 | 63 | 21 | 17 | 55 | 41 |
| Viscosity (5% in solution in DMF at 34.6° C.) | 1.55 | 1.49 | 1.42 | 1.51 | 1.56 | 1.41 |

EXAMPLES OF COMPOSITIONS

Example A

An aerosol lacquer was prepared according to the invention by mixing the following ingredients:

| | |
|---|---|
| Polymer prepared according to example 1 | 7.6 g |
| 2-amino 2-methyl 1-propanol sufficient for pH = 7 | |
| Ethanol sufficient for | 100 g |

22 g of the resulting composition was then packaged in an aerosol bomb with 78 g of a mixture of Freon 11/Freon 12, (61.5/38.5).

After application of this lacquer it was found that no powdering of the hair occurred in time.

Example B

An aerosol lacquer was prepared according to the invention by packaging in an aerosol bomb the following ingredients:

| | |
|---|---|
| Polymer prepared according to example 3 | 2 g |
| Ethanol | 40 g |
| Methylene Chloride | 20 g |
| 2-amino 2-methyl 1-propanol sufficient for pH = 7 | |
| Propellant: 35% propane/65% butane mixture | 40 g |

In this example the polymer prepared according to example 3 can advantageously be replaced by the same amount of one of the polymers prepared according to examples 4 to 6.

Example C

There was prepared according to the invention a setting lotion by mixing the following ingredients:

| | |
|---|---|
| Polymer prepared according to example 7 | 2 g |
| Perfume | 0.1 g |
| Ethanol | 45 g |
| 2-amino 2-methyl 1,3 propanediol sufficient for pH = 7 | |
| Water sufficient for | 100 g |

In this example, the copolymer prepared according to example 7 can advantageously be replaced by the same amount of one of the polymers prepared according to examples 8 to 12.

After this setting lotion was applied to hair previously washed with a shampoo, the hair was put up on setting rollers, then the hair was dried.

It was found that the setting lotion has a very good hold in time and that no powdering occurs. Moreover, the hair is not at all sticky even in an atmosphere with high humidity.

Example D

A setting lotion was prepared according to the invention by mixing the following ingredients:

| | |
|---|---|
| Polymer prepared according to example 13 | 2 g |
| Perfume | 0.2 g |
| Ethanol | 46 g |
| 2-amino 2-methyl 1,3-propanediol sufficient for pH = 7 | |
| Water sufficient for | 100 g |

In this example, the copolymer prepared according to example 13 can advantageously be replaced by the same amount of one of the polymers prepared according to examples 14 to 17 or 20.

After application of this setting lotion to hair, the latter was put up in setting rollers, then the hair was dried. It was found that the setting has a good hold in time and that no powdering occurs.

Example E

An aerosol lacquer according to the invention was prepared by packaging in an aerosol bomb the following ingredients:

| | |
|---|---|
| Polymer prepared according to example 18 | 2.3 g |
| Ethanol (or isopropanol) | 40 g |
| Methylene chloride | 20 g |
| 2-amino 2-methylene 1-propanol sufficient for pH = 7 | |
| Propellant: 35% propane/65% butane mixture | 40 g |

In this example, the polymer prepared according to example 18 can advantageously be replaced by the same amount of polymer prepared according to example 19 or example 21.

Example F

An aerosol lacquer according to the invention was prepared by mixing the following ingredients:

| | |
|---|---|
| Polymer prepared according to example 20 | 7.4 g |
| 2-amino 2-methyl 1-propanol sufficient for pH = 7 | |
| Ethanol (or isopropanol) sufficient for | 100 g |

22 of the resulting composition were then packaged in an aerosol bomb with 78 g of a mixture of Freon 11/Freon 12 (61.5/38.5).

When this lacquer was applied to hair, no powdering of the hair was noted in time and the hair, moreover, did not become sticky even in a humid atmosphere.

Example G

A setting lotion was prepared according to the invention by mixing the following ingredients:

| | |
|---|---|
| Polymer prepared according to example 3 | 3.5 g |
| Perfume | 0.1 g |
| Dye sufficient to color the lotion | 0.2 g |
| Isopropyl alcohol | 50 g |
| Water sufficient for | 100 g |

This setting lotion applied in the usual way made it possible to give the hair a shine and an excellent hold in time without formation of whitish films.

In this example, the copolymer prepared according to example 3 can advantageously be replaced by the same amount of one of the copolymers prepared according to examples 7, 8, 9 and 14.

Example H

Rinses were prepared according to the invention in emulsion form by mixing the following ingredients:

| | |
|---|---|
| Vaseline oil | 9.5 g |
| Fatty alcohol ($C_{16}$-$C_{18}$) polyglycerolated (2 to 6 moles) | 6.5 g |
| Polymer prepared according to example 6 | 1.5 g |
| Water sufficient for | 100 g |

This product was applied to washed and dried hair by carefully distributing it over all the hair and lightly massaging the hair.

After an application time of 2 minutes it was carefully rinsed.

The hair had a brilliant luster, was easy to untangle and no powdering effect was noted.

In this example the polymer prepared according to example 6 can be replaced by the same amount of one of the polymers prepared according to examples 10, 11, 12 and 15.

Example I

An anionic shampoo was prepared by mixing the following ingredients:

| | |
|---|---|
| Triethanolamine lauryl myristyl sulfate | 12 g |
| Copra diethanolamide | 2 g |
| Myristyldimethylamine oxide | 1.5 g |
| Polymer prepared according to example 13 | 1.5 g |
| Lactic acid sufficient for pH = 6.5 | |
| Water sufficient for | 100 g |

In this example the same amount of polymer according to example 13 can advantageously be replaced by a polymer obtained according to example 16 to 18.

Example J

A cationic shampoo according to the invention was prepared by mixing the following ingredients:

| | |
|---|---|
| Cetyltrimethylammonium bromide | 2 g |
| Lauric alcohol polyglycerolated with 4 moles of glycerol | 12 g |
| Polymer prepared according to example 19 | 1 g |
| Perfume | 0.2 g |
| Lactic acid sufficient for pH = 4.5 | |
| Water sufficient for | 100 ml |

In this example the copolymer according to example 19 can advantageously be replaced by the same amount of a polymer prepared according to example 20.

Example K

A nonionic shampoo according to the invention was prepared by mixing the following ingredients:

| | |
|---|---|
| Diol with $C_{11}$-$C_{14}$ polyglycerolated with 3-4 moles of glycerol | 17 g |
| Polymer prepared according to example 21 | 2 g |
| Cetyl pyridinium chloride | 0.8 g |
| Lauric diethanolamine | 2.5 g |
| Perfume | 0.2 g |
| Lactic acid sufficient for pH = 5.5 | |
| Water sufficient for | 100 ml |

In this example the polymer according to example 21 can be replaced by the same amount of a polymer obtained according to examples 7 to 12.

We claim:

1. A cosmetic composition containing in a suitable cosmetic vehicle at least one copolymer resulting from the copolymerization of:
   (i) 3 to 20% by weight of N-vinylpyrrolidone,
   (ii) 13 to 87% by weight of vinyl acetate,
   (iii) 2 to 15% by weight of crotonic acid, and
   (iv) 1 to 80% by weight of at least one fourth monomer selected from the group consisting of
   (a) a vinyl ester of the formula

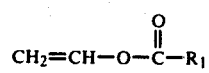

wherein, $R_1$ represents a linear or branched alkyl having 2–21 carbon atoms, (b) an allyl or methallyl ester of the formula

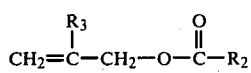

wherein, $R_2$ represents a linear or branched alkyl having 1–21 carbon atoms and $R_3$ represents hydrogen or methyl, (c) a vinyl ether of the formula $$CH_2=CH-O-R_4$$

wherein, $R_4$ represents a linear or branched alkyl having 4–18 carbon atoms, (d) an α-olefin of the formula $$CH_2=CH-(CH_2)_nCH_3$$

wherein, n is an integer from 3 to 15 inclusive, and (e) a vinyl, allyl or methallyl ester of an α- or β-cyclic carboxylic acid having the formula

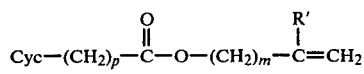

wherein, $R'$ represents hydrogen or methyl, m is 0 or 1, p is 0 or 1, when p is 0, Cyc represents a saturated or unsaturated mono- or polycyclic radical selected from

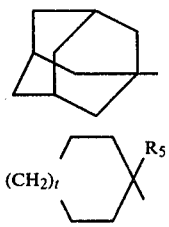  (i)

(ii)

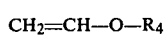

wherein, $R_5$ represents hydrogen or methyl and t is 0 or 1,

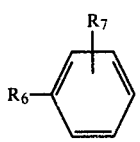  (iii)

wherein, $R_6$ is hydrogen, methyl, ethyl, tert.-butyl, ethoxy, or dodecoxy and $R_7$ is hydrogen, alkyl having 1–4 carbon atoms or alkoxy having 1–4 carbon atoms, or

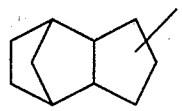  (iv)

and when p is 1, Cyc represents

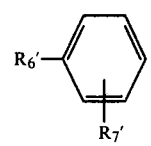

wherein, $R'_6$ and $R'_7$ have the same meanings as $R_6$ and $R_7$ given above.

2. The composition of claim 1 wherein said fourth monomer is a vinyl, allyl or methallyl ester of 1-adamantane carboxylic acid, cyclohexane carboxylic acid, cyclopentane carboxylic acid, benzoic acid, phenylacetic acid, 4-tert.-butyl benzoic acid, cyclopentane 1-methyl carboxylic acid, cyclohexane 1-methyl carboxylic acid, tricyclo decane 3-carboxylic acid and tricyclo decane 4-carboxylic acid and their mixtures.

3. The composition of claim 1 wherein the copolymer corresponds to the following general formula:

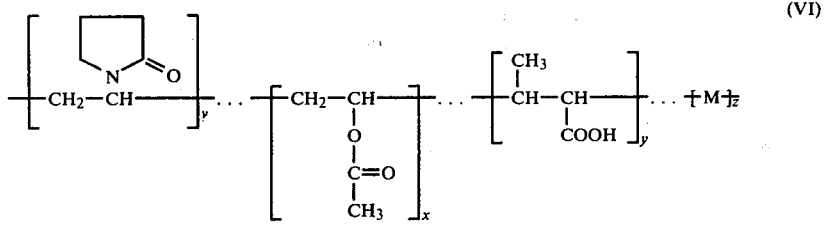  (VI)

wherein:

M represents a group of at least one unsaturated monomer according to formulas in (a)–(e) of claim 1 v representing from 1 to 30% by weight, x representing from 13 to 87% by weight, y representing from 2 to 15% by weight, and z representing from 1 to 80% by weight, v+x+y+z being equal to 100%.

4. The composition of claim 1 wherein the copolymer is in a form neutralized by an inorganic or organic base selected from the group consisting of soda, potash, ammonia, monoethanolamine, diethanolamine, triethanolamine, isopropanolamine, diisopropanolamine, triamine, 2-amino 2-methyl 1-propanol, 2-amino 2-methyl 1,3-propanediol and 2-amino 2-hydroxymethyl 1,3-propanediol, said neutralization being total or partial.

5. The composition of claim 1 containing from 0.5 to 10% by weight of said copolymer.

6. The composition of claim 1 in the form of an aqueous or dilute alcohol solution containing from 20 to 70% alcohol, said copolymer being present in an amount between 1 to 3% by weight.

7. The composition of claim 1 in the form of a solution in an alcohol in admixture with a propellant and packaged in an aerosol bomb, said copolymer being present in an amount between 0.7 and 8% by weight.

8. The composition of claim 7 wherein the alcohol is ethanol or isopropanol.

9. The composition of claim 7 which includes a third solvent in an amount between 3 to 35% by weight relative to the total weight of the composition.

10. The composition of claim 1 which also contains another polymer of anionic or cationic nature in an amount between 0.01 and 10% by weight thereof.

11. The cosmetic composition of claim 10 wherein said another polymer is present in an amount between 0.02 and 5% by weight thereof.

12. The cosmetic composition of claim 1 which also includes an effective amount of at least one adjuvant selected from a plasticizer, a glossing agent, a perfume, a dye, a restructuring agent or an anionic, cationic or nonionic surfactant.

* * * * *

UNITED STATES PATENT AND TRADEMARK OFFICE
CERTIFICATE OF CORRECTION

PATENT NO. : 4,272,511

DATED : June 9, 1981

INVENTOR(S) : Christos Papantoniou et al.

It is certified that error appears in the above-identified patent and that said Letters Patent is hereby corrected as shown below:

Column 11, line 66, after "oxy," insert -- butoxy --.

Signed and Sealed this

Twenty-third Day of November 1982

[SEAL]

Attest:

GERALD J. MOSSINGHOFF

Attesting Officer — Commissioner of Patents and Trademarks

UNITED STATES PATENT AND TRADEMARK OFFICE
CERTIFICATE OF CORRECTION

PATENT NO. : 4,272,511
DATED : June 9, 1981
INVENTOR(S) : Christos Papantoniou and Jean Mondet It is certified that error appears in the above—identified patent and that said Letters Patent is hereby corrected as shown below:

Col. 2, between lines 60 and 67, the structural formula should read

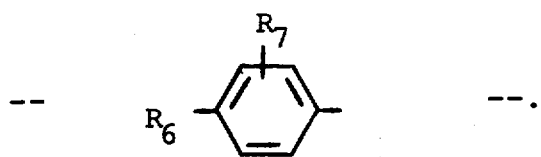

Col. 11, between lines 57 and 65, the structural formula should read

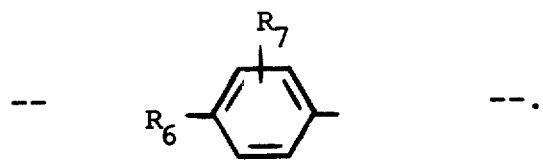

Signed and Sealed this

Eighth Day of March 1983

[SEAL]

Attest:

GERALD J. MOSSINGHOFF

Attesting Officer   Commissioner of Patents and Trademarks